(12) United States Patent
She et al.

(10) Patent No.: US 12,292,411 B2
(45) Date of Patent: May 6, 2025

(54) DEVICE AND METHOD FOR MEASURING BONDING STRENGTH BETWEEN CONTAMINATED ROCK SURFACE AND SOLIDIFIED MATERIAL

(71) Applicant: Chengdu University Of Technology, Chengdu (CN)

(72) Inventors: Jiping She, Chengdu (CN); Yunfei Wang, Chengdu (CN); Furong Gong, Chengdu (CN); Wenjing Ma, Chengdu (CN); Shiyu Zhang, Chengdu (CN); Gege Teng, Chengdu (CN); Huimin Li, Chengdu (CN)

(73) Assignee: Chengdu University Of Technology, Chengdu (CN)

( * ) Notice: Subject to any disclaimer, the term of this patent is extended or adjusted under 35 U.S.C. 154(b) by 0 days.

(21) Appl. No.: 18/888,210

(22) Filed: Sep. 18, 2024

(65) Prior Publication Data

US 2025/0093244 A1 Mar. 20, 2025

(30) Foreign Application Priority Data

Sep. 19, 2023 (CN) .......................... 202311208480.6

(51) Int. Cl.
*G01N 3/02* (2006.01)
*G01N 33/24* (2006.01)

(52) U.S. Cl.
CPC ............... *G01N 3/02* (2013.01); *G01N 33/24* (2013.01)

(58) Field of Classification Search
CPC .......... G01N 19/04; G01N 29/04; G01N 3/24; G01N 3/02; G01N 33/24; E02D 3/12;

(Continued)

(56) References Cited

U.S. PATENT DOCUMENTS 5,546,797 A 8/1996 Dutta et al.
2018/0031457 A1 2/2018 Jiang et al.

FOREIGN PATENT DOCUMENTS

CN 1664547 A 9/2005
CN 2783312 Y 5/2006

(Continued)

OTHER PUBLICATIONS

Shen Jianwen, et al., Fracture gas invasion mechanism and plugging method of shale gas layer, Journal of Chengdu University of Technology, 2022, pp. 579-585, vol. 49 No. 5.

(Continued)

*Primary Examiner* — Brandi N Hopkins
(74) *Attorney, Agent, or Firm* — Bayramoglu Law Offices LLC

(57) ABSTRACT

The provided are a device and method for measuring a bonding strength between a contaminated rock surface and a solidified material. The device includes a fixing and measuring assembly and four rock slabs enclosing a rectangular prism, where outer surfaces of the four rock slabs are fitted to two transverse support plates and two longitudinal support plates, respectively; the two longitudinal support plates are arranged between the two transverse support plates; upper and lower ends of the rock slabs are provided with an upper cover and a bottom plate, respectively; the upper cover and the bottom plate are detachably fixed to the two transverse support plates, respectively; the two transverse support plates are detachably fixed to each other through a second screw; a hydraulic device is provided among the four posts; and a movable end of the hydraulic device is provided with a supporting airbag.

20 Claims, 2 Drawing Sheets

(58) Field of Classification Search
CPC ...... E21D 9/001; C09J 177/08; C04B 41/009; A61C 13/20; B05D 7/54; B28B 11/04
See application file for complete search history.

(56) References Cited

FOREIGN PATENT DOCUMENTS

| | | | | |
|---|---|---|---|---|
| CN | 203798714 | U | | 8/2014 |
| CN | 104406910 | A | | 3/2015 |
| CN | 105092465 | A | | 11/2015 |
| CN | 105403505 | A | | 3/2016 |
| CN | 205538625 | U | | 8/2016 |
| CN | 106596400 | A | | 4/2017 |
| CN | 206609732 | U | | 11/2017 |
| CN | 108152143 | A | | 6/2018 |
| CN | 108663319 | A | | 10/2018 |
| CN | 109085117 | A | | 12/2018 |
| CN | 109540788 | A | | 3/2019 |
| CN | 110470596 | A | | 11/2019 |
| CN | 107179396 | B | * | 1/2020 ............ G01N 33/24 |
| CN | 111504898 | A | | 8/2020 |
| CN | 211516003 | U | * | 9/2020 |
| CN | 211528184 | U | | 9/2020 |
| CN | 112082875 | A | | 12/2020 |
| CN | 212111082 | U | | 12/2020 |
| CN | 109540788 | B | * | 2/2021 ............ G01N 19/04 |
| CN | 113109181 | A | | 7/2021 |
| CN | 214251753 | U | | 9/2021 |
| CN | 113777029 | A | | 12/2021 |
| CN | 115929287 | A | | 4/2023 |
| CN | 218884955 | U | | 4/2023 |
| JP | 2002250683 | A | | 9/2002 |

OTHER PUBLICATIONS

Zheng Lihui, et al., Novel low-density drilling fluid containing fuzzy ball structure, Acta Petrolei Sinica, 2010, pp. 490-493, vol. 31 No. 3.

Ying Zhong, et al., A composite temporary plugging technology for hydraulic fracture diverting treatment in gas shales: Using degradable particle/powder gels (DPGs) and proppants as temporary plugging agents, Journal of Petroleum Science and Engineering, 2022, pp. 1-11, vol. 216, 110851.

Sajjad Mozaffari, et al., Oil-well lightweight cement slurry for improving compressive strength and hydration rate in low-temperature conditions, Construction and Building Materials, 2022, pp. 1-10, vol. 357, 129301.

* cited by examiner

DEVICE AND METHOD FOR MEASURING BONDING STRENGTH BETWEEN CONTAMINATED ROCK SURFACE AND SOLIDIFIED MATERIAL

CROSS-REFERENCE TO THE RELATED APPLICATIONS

This application is based upon and claims priority to Chinese Patent Application No. 202311208480.6, filed on Sep. 19, 2023, the entire contents of which are incorporated herein by reference.

TECHNICAL FIELD

The present disclosure relates to the field of oil and natural gas exploration and development, and in particular to a device and method for measuring a bonding strength between a contaminated rock surface and a solidified material.

BACKGROUND

Drilling fluid is a general term for various circulating fluids that meet the needs of drilling work with multiple functions during the drilling process. Drilling fluid will leak when encountering karst formations, natural or induced fractures, or high-permeability formations during the drilling process. The conventional method to prevent further leakage of drilling fluid is to use a lost circulation material to seal off the target formation. There is a lost circulation material called solidified material, which is bonded to the fractured rock surface to achieve the sealing purpose. In this case, cementing slurry is first prepared according to a specific formula, and then solidifies to form the solidified material under the temperature and pressure of the formation to effectively seal the fracture. It is necessary to design a device for performing laboratory simulation on the drilling fluid that contaminates the rock surface under formation conditions and performing laboratory testing of the bonding strength between the rock surface and the solidified material. This is of great significance to evaluate the sealing effect of the lost circulation material in the formation and select the lost circulation material. However, the current laboratory devices for testing the bonding strength of solidified materials have the following problems.

1. In actual operation, the fracture is sealed only after the drilling fluid leaks, that is, the target rock surface has been contaminated by the drilling fluid. However, during laboratory testing, the rock slab is not contaminated by the drilling fluid, resulting in a deviation between the tested bonding strength of the solidified material and actual situation.

2. The existing device does not use the real rock slab from the formation as the wall, but directly conducts solidification and bonding strength testing inside the metal instrument. Therefore, there is a significant deviation between the test result and actual situation, affecting the selection of the lost circulation material.

3. Currently, the instrument does not simulate the pressurization state in the solidification process of the cementing slurry, so the test results are inconsistent with that under the formation temperature and pressure.

4. Currently, regarding the measurement of the bonding strength, the partition is directly pushed by means of hydraulic or mechanical pressure, and then the solidified material is pushed to measure the bonding strength. If the partition comes into contact with the wall, the frictional resistance between the partition and the wall cannot be offset, resulting in an error between the measured strength and the actual value. If the partition does not come into contact with the wall (not completely covering the solidified material), it may cause tearing of the solidified material during the pushing process.

5. The contaminated rock surface is uneven. Therefore, similar to Problem 4, when the partition is directly pushed, the partition may be pushed along with the material attached to the contaminated rock surface (not only the solidified material is pushed). Besides, it may cause tearing of the solidified material.

SUMMARY

In view of the above shortcomings of the prior art, the present disclosure provides a device and method for measuring a bonding strength between a contaminated rock surface and a solidified material. The present disclosure solves the problem that the existing device is hard to accurately measure the cementing strength between the solidified material and the contaminated rock surface.

To achieve the above objective, the present disclosure adopts the following technical solutions:

The device for measuring a bonding strength between a contaminated rock surface and a solidified material includes a fixing and measuring assembly and four rock slabs enclosing a rectangular prism, where outer surfaces of the four rock slabs are fitted to two transverse support plates and two longitudinal support plates, respectively; the two longitudinal support plates are arranged between the two transverse support plates; upper and lower ends of the rock slabs are provided with an upper cover and a bottom plate, respectively; the upper cover and the bottom plate are detachably fixed to the two transverse support plates, respectively; the two transverse support plates are detachably fixed to each other through a second screw; two ends of each of the transverse support plates are provided with limit plates; the limit plates each are provided with a second threaded hole that matches a third screw; and the third screw is configured to support the longitudinal support plate;

the upper cover is provided with a feeding port and a motor; the motor is configured to drive an agitator through a coupling; when working, the agitator is located within a space enclosed by the four rock slabs; and the bottom plate is provided with a discharge port;

the fixing and measuring assembly includes four posts that enclose a rectangular prism; a crossbar is provided between each two adjacent posts; the crossbar is connected to an L-shaped clip through a telescopic rod; a hydraulic device is provided among the four posts; and a movable end of the hydraulic device is provided with a supporting airbag;

the L-shaped clip is configured to restrict the upward or transverse movement of the transverse support plate, the longitudinal support plate, and the rock slab during the measurement of the bonding strength between the contaminated rock surface and the solidified material;

the hydraulic device is configured to provide a jacking force during the measurement of the bonding strength between the contaminated rock surface and the solidified material; and the supporting airbag is configured to come into contact with the solidified material and push the solidified material upwards during the measurement of the bonding strength between the contaminated rock surface and the solidified material.

Further, longitudinal first mounting slots are arranged at left and right sides of the upper cover, respectively; upper surfaces of the two transverse support plates are provided with first threaded holes; a front end of a first screw passes through the first mounting slot of the upper cover and matches the first threaded hole, such that the upper cover is detachably fixed to the transverse support plate; and a length of the first mounting slot is greater than a length of the longitudinal support plate.

Further, longitudinal second mounting slots are arranged at left and right sides of the bottom plate, respectively; lower surfaces of the two transverse support plates are provided with third threaded holes; a front end of a fourth screw passes through the second mounting slot of the bottom plate and matches the third threaded hole, such that the bottom plate is detachably fixed to the transverse support plate; and a length of the second mounting slot is greater than a length of the longitudinal support plate.

Further, sealing strips are provided between the transverse support plate and the longitudinal support plate, between the transverse support plate and the bottom plate, between the transverse support plate and the upper cover, and between the upper cover and the longitudinal support plate.

Further, the transverse support plates and the longitudinal support plates each are provided with a heating coil.

The method for measuring a bonding strength between a contaminated rock surface and a solidified material is based on the device for measuring a bonding strength between a contaminated rock surface and a solidified material, and includes the following steps:

S1: forming a measurement space: enclosing, by the four rock slabs, the rectangular prism; arranging the longitudinal support plates behind longitudinal rock slabs, and arranging the transverse support plate behind transverse rock slabs; fixing, through the second screws, the two transverse support plates; fixing the upper cover and the bottom plate to the transverse support plates; and supporting, through the third screws, the longitudinal support plates;

S2: contaminating, by a drilling fluid, the rock slabs; closing the discharge port, and injecting the drilling fluid into the measurement space; pressurizing, through the feeding port, the measurement space; and starting the motor to drive the agitator for stirring;

S3: stopping the pressurization; opening the discharge port to discharge the drilling fluid; removing the bottom plate, and taking out the agitator; laying an isolation film on an upper surface of the bottom plate; and fixing the bottom plate to the transverse support plates;

S4: injecting a cementing liquid into the measurement space from the feeding port; and pressurizing, through the feeding port, the measurement space until the cementing liquid solidifies to form the solidified material.

S5: stopping the pressurization; removing the upper cover; clamping, through the L-shaped clips, upper ends of the transverse support plates, the longitudinal support plates, and the rock slabs; and removing the bottom plate;

S6: placing the hydraulic device directly below the solidified material, and applying a lubricant to a surface of the supporting airbag;

S7: starting the hydraulic device to bring the supporting airbag into contact with the solidified material and push the solidified material upwards; and recording a thrust of the hydraulic device until the solidified material moves relative to the rock slab; and S8: acquiring the bonding strength between the contaminated rock surface and the solidified material based on the recorded thrust of the hydraulic device.

Further, in the step S4, a temperature during solidification of the cementing liquid is increased by the heating coils.

Further, in the step S1, contact positions between each two adjacent rock slabs are bonded with glue, such that the four rock slabs enclose the rectangular prism.

The present disclosure has the following beneficial effects:

1. The device for measuring uses real rock slabs for contamination and measures the bonding strength between the contaminated rock slab and the solidified material, which is in line with the actual situation.

2. The upper cover and the bottom plate of the device for measuring can be disassembled for easy contamination, cementing, and pushing of the solidified material.

3. The device for measuring can provide strong support for the rock slab, making it easy to simulate the formation environment by applying pressure and heating.

4. The device for measuring uses an airbag as the thrust medium. The airbag has a certain degree of flexibility around it, and can cross the rough contaminated rock surface, thereby steadily pushing the solidified material while avoiding damaging the contaminated rock surface. A lubricant is added to reduce the frictional force between the airbag and the contaminated rock surface, and improve the accuracy of bonding strength measurement.

5. In the method for measuring, the size of the measurement space remains unchanged from the step of contaminating the rock slab to the end of the final measurement. The upper cover can be disassembled at different stages without affecting the ejection of the solidified material. The bottom plate is disassembled before the cementing liquid is injected into the measurement space, such that the agitator can be removed to avoid affecting the solidified material. Meanwhile, an isolation film can be laid to prevent the bonding between the bottom plate and the solidified material, and to prevent damage to the solidified material when the bottom plate is disassembled. The design reduces the impact of the entire measurement process on the solidified material.

6. The method for measuring uses an L-shaped clip to secure the support plate, ensuring that the entire measurement space remains stable when the hydraulic device applies force, and guaranteeing the accuracy of thrust.

Figure 1:
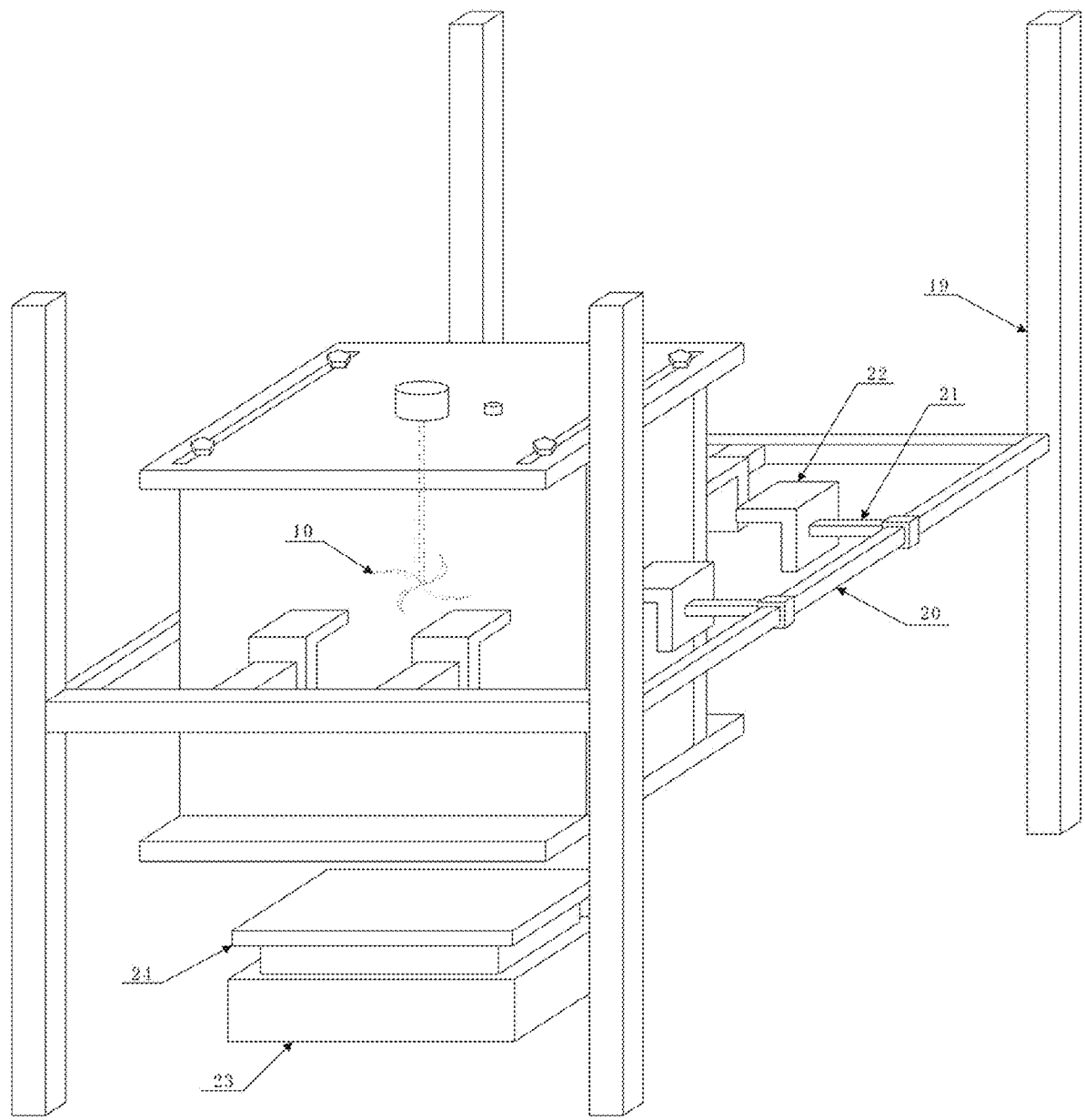
FIG. 1 is an overall structural diagram of a device according to the present disclosure.

REFERENCE NUMERALS 1. upper cover; 2. transverse support plate; 3. longitudinal support plate; 4. rock slab; 5. bottom plate; 6. motor; 7. feeding port; 8. first mounting slot; 9. first screw; 10. agitator; 11. second screw; 12. first threaded hole; 13. limit plate; 14. second threaded hole; 15. third screw; 16. discharge port; 17. second mounting slot; 18. fourth screw; 19. post; 20. crossbar; 21. telescopic rod; 22. L-shaped clip; 23. hydraulic device; and 24. supporting airbag.

DETAILED DESCRIPTION OF THE EMBODIMENTS

The specific embodiment of the present disclosure will be described below so that those skilled in the art can understand the present disclosure, but it should be clear that the present disclosure is not limited to the scope of the specific embodiment. For those of ordinary skill in the art, as long as various changes fall within the spirit and scope of the present disclosure defined and determined by the appended claims, these changes are apparent, and all inventions and creations using the concept of the present disclosure are protected.

Figure 2:
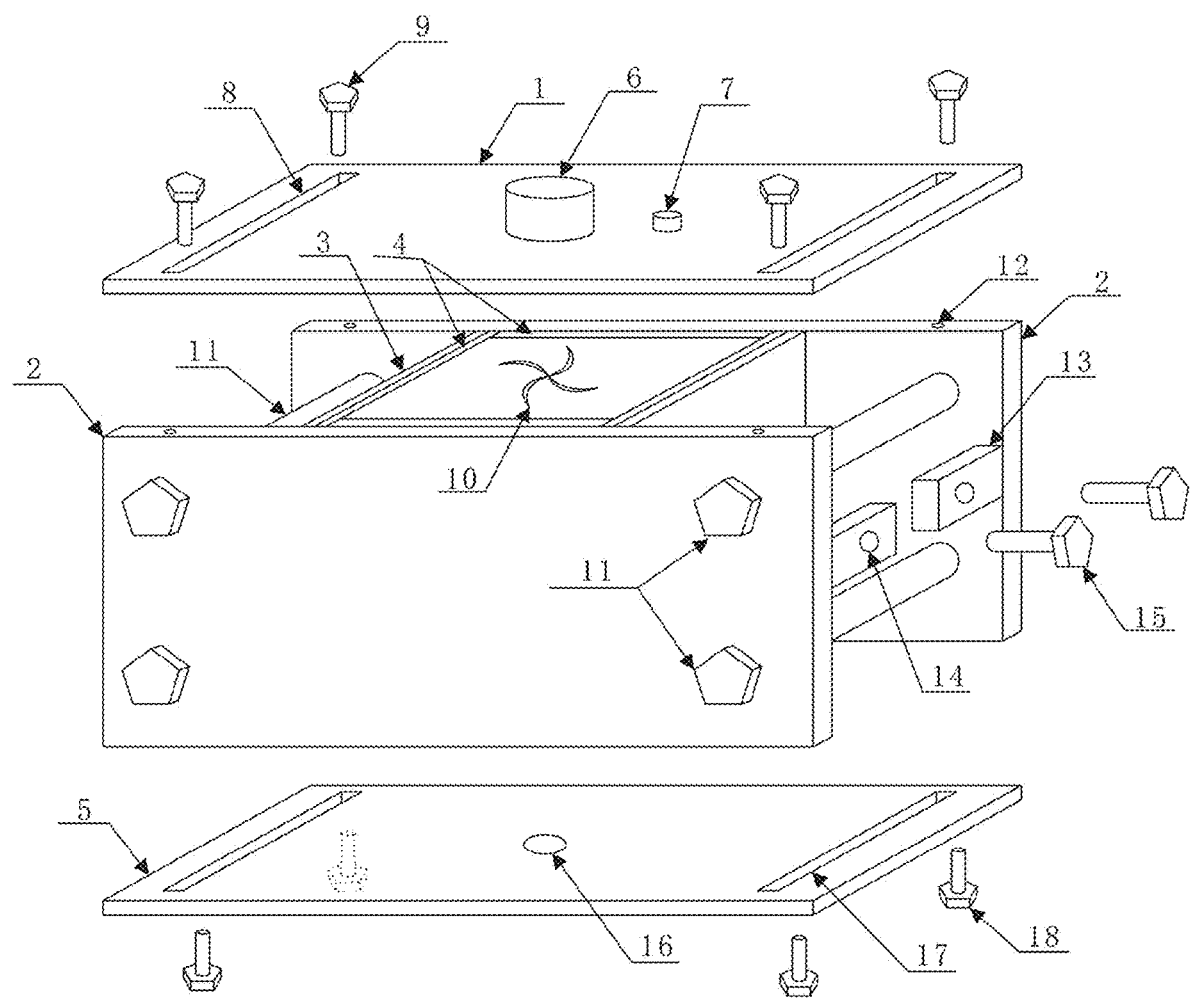
FIG. 2 is a partial exploded view of the device according to the present disclosure.

As shown in FIGS. 1 and 2, a device for measuring a bonding strength between a contaminated rock surface and a solidified material includes a fixing and measuring assembly and four rock slabs 4 enclosing a rectangular prism. Outer surfaces of the four rock slabs 4 are fitted to two transverse support plates 2 and two longitudinal support plates 3, respectively. The two longitudinal support plates 3 are arranged between the two transverse support plates 2. Upper and lower ends of the rock slabs 4 are provided with upper cover 1 and bottom plate 5, respectively. The upper cover 1 and the bottom plate 5 are detachably fixed to the two transverse support plates 2, respectively. The two transverse support plates 2 are detachably fixed to each other through second screw 11. Two ends of each of the transverse support plates 2 are provided with limit plates 13. The limit plates 13 each are provided with second threaded hole 14 that matches third screw 15. The third screw 15 is configured to support the longitudinal support plate 3.

The upper cover 1 is provided with feeding port 7 and motor 6. The motor 6 is configured to drive agitator 10 through a coupling. When working, the agitator 10 is located within a space enclosed by the four rock slabs 4. The bottom plate 5 is provided with discharge port 16.

The fixing and measuring assembly includes four posts 19 that enclose a rectangular prism. Crossbar 20 is provided between each two adjacent posts 19. The crossbar 20 is connected to L-shaped clip 22 through telescopic rod 21. Hydraulic device 23 is provided among the four posts 19. A movable end of the hydraulic device 23 is provided with supporting airbag 24.

The L-shaped clip 22 is configured to restrict the upward or transverse movement of the transverse support plate 2, the longitudinal support plate 3, and the rock slab 4 during the measurement of the bonding strength between the contaminated rock surface and the solidified material.

The hydraulic device 23 is configured to provide a jacking force during the measurement of the bonding strength between the contaminated rock surface and the solidified material.

The supporting airbag 24 is configured to come into contact with the solidified material and push the solidified material upwards during the measurement of the bonding strength between the contaminated rock surface and the solidified material.

Longitudinal first mounting slots 8 are arranged at left and right sides of the upper cover 1, respectively. Upper surfaces of the two transverse support plates 2 are provided with first threaded holes 12. A front end of first screw 9 passes through the first mounting slot 8 of the upper cover 1 of the upper cover and matches the first threaded hole 12, such that the upper cover 1 is detachably fixed to the transverse support plate 2. A length of the first mounting slot 8 is greater than a length of the longitudinal support plate 3.

Longitudinal second mounting slots 17 are arranged at left and right sides of the bottom plate 5, respectively. Lower surfaces of the two transverse support plates 2 are provided with third threaded holes. A front end of fourth screw 18 passes through the second mounting slot 17 of the bottom plate 5 and matches the third threaded hole, such that the bottom plate 5 is detachably fixed to the transverse support plate 2. A length of the second mounting slot 17 is greater than a length of the longitudinal support plate 3.

Sealing strips are provided between the transverse support plate 2 and the longitudinal support plate 3, between the transverse support plate 2 and the bottom plate 5, between the transverse support plate 2 and the upper cover 1, and between the upper cover 1 and the longitudinal support plate 3. The transverse support plates 2 and the longitudinal support plates 3 each are provided with a heating coil.

A method for measuring a bonding strength between a contaminated rock surface and a solidified material includes the following steps.

S1. A measurement space is formed. The four rock slabs 4 are bonded with glue to form the rectangular prism. The longitudinal support plates 3 are arranged behind longitudinal rock slabs 4, and the transverse support plate 2 are arranged behind transverse rock slabs 4. The two transverse support plates 2 are fixed through the second screws 11. The upper cover 1 and the bottom plate 5 are fixed to the transverse support plates 2. The third screws 15 support the longitudinal support plates 3.

S2. The rock slabs 4 are contaminated by a drilling fluid. The discharge port 16 is closed, and the drilling fluid is injected into the measurement space. The measurement space is pressurized through the feeding port 7, and the motor 6 is started to drive the agitator 10 for stirring.

S3. The pressurization is stopped. The discharge port 16 is opened to discharge the drilling fluid. The bottom plate 5 is removed, and the agitator 10 is taken out. An isolation film is laid on an upper surface of the bottom plate 5, and the bottom plate 5 is fixed to the transverse support plates 2.

S4. A cementing liquid is injected into the measurement space from the feeding port 7, and the measurement space is pressurized through the feeding port 7 until the cementing liquid solidifies to form the solidified material.

S5. The pressurization is stopped. The upper cover 1 is removed, and upper ends of the transverse support plates 2, the longitudinal support plates 3, and the rock slabs 4 are clamped through the L-shaped clips 22. The bottom plate 5 is removed.

S6. The hydraulic device 23 is placed directly below the solidified material, and a lubricant is applied to a surface of the supporting airbag 24.

S7. The hydraulic device 23 is started to bring the supporting airbag 24 into contact with the solidified material and push the solidified material upwards, and a thrust of the hydraulic device 23 is recorded until the solidified material moves relative to the rock slab 4.

S8. The bonding strength between the contaminated rock surface and the solidified material is acquired based on the recorded thrust of the hydraulic device 23.

In the step S1, contact positions between each two adjacent rock slabs 4 are bonded with glue, such that the four rock slabs 4 enclose the rectangular prism. In the step S4, the temperature during solidification of the cementing liquid is increased by the heating coils.

In an embodiment of the present disclosure, the transverse support plates 2, the longitudinal support plates 3, the upper cover 1, and the bottom plate 5 all are steel plates to provide sufficient rigidity. One transverse support plate 2 is provided with a hole for the second screw 11 to pass through, which is a regular through-hole, and the other transverse support plate 2 is provided with a hole that matches the second screw 11, which is a threaded hole. The distance between the two transverse support plates 2 is adjusted by turning the second screws 11.

The first mounting slots 8 support the upper cover 1 to adapt to different distances between the transverse support plates 2, improving the utilization of components. Similarly, the second mounting slots 17 support the bottom plate 5 to adapt to different distances between the transverse support plates 2.

In a specific implementation process, the size of the supporting airbag 24 is slightly smaller than that of the measurement space, that is, the size of the supporting airbag 24 approximates that of the contaminated measurement space. The jacking surface of the hydraulic device 23 is slightly smaller than the size of the supporting airbag 24, providing a cushioning space around the supporting airbag 24. The design facilitates sliding over the uneven contaminated rock surface by a local depression means without affecting the push of the solidified material.

In order to further reduce the influence of the frictional force between the supporting airbag 24 and the contaminated rock surface on the measurement, after acquiring the thrust data of the hydraulic device 23 by the method for measuring, the solidified material is taken out of the measurement space and varying squeezing forces are applied to the upper surface of the supporting airbag 24 to acquire the frictional force between the supporting airbag 24 and the contaminated rock surface under the different squeezing forces. Curve fitting of the frictional force curve is performed to acquire a corresponding relationship between the frictional force between the supporting airbag 24 and the contaminated rock surface under different squeezing forces. The corresponding relationship is corrected based on the thrust data of the hydraulic device 23, thereby correcting the bonding strength between the solidified material and the contaminated rock surface. The squeezing force can be applied by placing a heavy object. The heavy object does not come into contact with the contaminated rock surface, and the size of the heavy object is slightly smaller than the measurement space. For example, the solidified material is pushed when the thrust of the hydraulic device 23 is X Newtons. Then, when the supporting airbag 24 is pushed to move relative to the contaminated rock surface in case of a heavy object of (X/g) kilograms, a thrust of Y Newtons is derived, and the corrected bonding strength between the solidified material and the contaminated rock surface is calculated as (2X-Y-mg) Newtons, where m is the mass of the solidified material, measured in kilograms, and g is the acceleration due to gravity.

In summary, the present disclosure uses real rock slabs for contamination and employs an airbag as the thrust medium to stably push the solidified material while avoiding damage to the contaminated rock surface. The present disclosure measures the bonding strength between the contaminated rock slab and the solidified material, improving the accuracy of bonding strength measurement.

What is claimed is:

1. A device for measuring a bonding strength between a contaminated rock surface and a solidified material, comprising a fixing and measuring assembly and four rock slabs enclosing a first rectangular prism, wherein outer surfaces of the four rock slabs are fitted to two transverse support plates and two longitudinal support plates, respectively; the two longitudinal support plates are arranged between the two transverse support plates; upper and lower ends of the rock slabs are provided with an upper cover and a bottom plate, respectively; the upper cover and the bottom plate are detachably fixed to the two transverse support plates, respectively; the two transverse support plates are detachably fixed to each other through a second screw; two ends of each of the transverse support plates are provided with limit plates; the limit plates each are provided with a second threaded hole, and the second threaded hole matches a third screw; and the third screw is configured to support the longitudinal support plate;
   the upper cover is provided with a feeding port and a motor; the motor is configured to drive an agitator through a coupling; when working, the agitator is located within a space enclosed by the four rock slabs; and the bottom plate is provided with a discharge port;
   the fixing and measuring assembly comprises four posts, and the four posts enclose a second rectangular prism; a crossbar is provided between each two adjacent posts; the crossbar is connected to an L-shaped clip through a telescopic rod; a hydraulic device is provided among the four posts; and a movable end of the hydraulic device is provided with a supporting airbag;
   the L-shaped clip is configured to restrict upward or transverse movement of the transverse support plate, the longitudinal support plate, and the rock slab during the measurement of the bonding strength between the contaminated rock surface and the solidified material;
   the hydraulic device is configured to provide a jacking force during the measurement of the bonding strength between the contaminated rock surface and the solidified material; and
   the supporting airbag is configured to come into contact with the solidified material and push the solidified material upwards during the measurement of the bonding strength between the contaminated rock surface and the solidified material;
   wherein a size of the supporting airbag is slightly smaller than a size of a measurement space, wherein the size of the supporting airbag approximates a size of a contaminated measurement space; a jacking surface of the hydraulic device is slightly smaller than the size of the supporting airbag, providing a cushioning space around the supporting airbag; the design facilitates sliding over the uneven contaminated rock surface by a local depression means without affecting a push of the solidified material.

2. The device for measuring the bonding strength between the contaminated rock surface and the solidified material according to claim 1, wherein longitudinal first mounting slots are arranged at left and right sides of the upper cover, respectively; upper surfaces of the two transverse support plates are provided with first threaded holes; a front end of a first screw passes through the first mounting slot of the upper cover and matches the first threaded hole, wherein the upper cover is detachably fixed to the transverse support plate; and a length of the first mounting slot is greater than a length of the longitudinal support plate.

3. The device for measuring the bonding strength between the contaminated rock surface and the solidified material according to claim 1, wherein longitudinal second mounting slots are arranged at left and right sides of the bottom plate, respectively; lower surfaces of the two transverse support plates are provided with third threaded holes; a front end of a fourth screw passes through the second mounting slot of the bottom plate and matches the third threaded hole, wherein the bottom plate is detachably fixed to the transverse support plate; and a length of the second mounting slot is greater than a length of the longitudinal support plate.

4. The device for measuring the bonding strength between the contaminated rock surface and the solidified material according to claim 1, wherein sealing strips are provided between the transverse support plate and the longitudinal support plate, between the transverse support plate and the bottom plate, between the transverse support plate and the upper cover, and between the upper cover and the longitudinal support plate.

5. The device for measuring the bonding strength between the contaminated rock surface and the solidified material according to claim 1, wherein the transverse support plates and the longitudinal support plates each are provided with a heating coil.

6. A method for measuring a bonding strength between a contaminated rock surface and a solidified material, based on the device for measuring the bonding strength between the contaminated rock surface and the solidified material according to claim 1, and comprising the following steps:

S1: forming the measurement space: enclosing, by the four rock slabs, the first rectangular prism; arranging the longitudinal support plates behind longitudinal rock slabs, and arranging the transverse support plate behind transverse rock slabs; fixing, through the second screws, the two transverse support plates; fixing the upper cover and the bottom plate to the transverse support plates; and supporting, through the third screws, the longitudinal support plates;

S2: contaminating, by a drilling fluid, the rock slabs; closing the discharge port, and injecting the drilling fluid into the measurement space; pressurizing, through the feeding port, the measurement space; and starting the motor to drive the agitator for stirring;

S3: stopping the pressurization; opening the discharge port to discharge the drilling fluid; removing the bottom plate, and taking out the agitator; laying an isolation film on an upper surface of the bottom plate; and fixing the bottom plate to the transverse support plates;

S4: injecting a cementing liquid into the measurement space from the feeding port; and pressurizing, through the feeding port, the measurement space until the cementing liquid solidifies to form the solidified material;

S5: stopping the pressurization; removing the upper cover; clamping, through the L-shaped clips, upper ends of the transverse support plates, the longitudinal support plates, and the rock slabs; and removing the bottom plate;

S6: placing the hydraulic device directly below the solidified material, and applying a lubricant to a surface of the supporting airbag;

S7: starting the hydraulic device to bring the supporting airbag into contact with the solidified material and push the solidified material upwards; and recording a thrust of the hydraulic device until the solidified material moves relative to the rock slab; and S8: acquiring the bonding strength between the contaminated rock surface and the solidified material based on the recorded thrust of the hydraulic device.

7. The method for measuring the bonding strength between the contaminated rock surface and the solidified material according to claim 6, wherein in the step S4, a temperature during solidification of the cementing liquid is increased by heating coils.

8. The method for measuring the bonding strength between the contaminated rock surface and the solidified material according to claim 6, wherein in the step S1, contact positions between each two adjacent rock slabs are bonded with glue, wherein the four rock slabs enclose the first rectangular prism.

9. The method according to claim 6, wherein in the device for measuring the bonding strength between the contaminated rock surface and the solidified material, longitudinal first mounting slots are arranged at left and right sides of the upper cover, respectively; upper surfaces of the two transverse support plates are provided with first threaded holes; a front end of a first screw passes through the first mounting slot of the upper cover and matches the first threaded hole, wherein the upper cover is detachably fixed to the transverse support plate; and a length of the first mounting slot is greater than a length of the longitudinal support plate.

10. The method for measuring the bonding strength between the contaminated rock surface and the solidified material according to claim 9, wherein in the step S4, a temperature during solidification of the cementing liquid is increased by heating coils.

11. The method for measuring the bonding strength between the contaminated rock surface and the solidified material according to claim 9, wherein in the step S1, contact positions between each two adjacent rock slabs are bonded with glue, wherein the four rock slabs enclose the first rectangular prism.

12. The method according to claim 6, wherein in the device for measuring the bonding strength between the contaminated rock surface and the solidified material, longitudinal second mounting slots are arranged at left and right sides of the bottom plate, respectively; lower surfaces of the two transverse support plates are provided with third threaded holes; a front end of a fourth screw passes through the second mounting slot of the bottom plate and matches the third threaded hole, wherein the bottom plate is detachably fixed to the transverse support plate; and a length of the second mounting slot is greater than a length of the longitudinal support plate.

13. The method for measuring the bonding strength between the contaminated rock surface and the solidified material according to claim 12, wherein in the step S4, a temperature during solidification of the cementing liquid is increased by heating coils.

14. The method for measuring the bonding strength between the contaminated rock surface and the solidified material according to claim 12, wherein in the step S1, contact positions between each two adjacent rock slabs are bonded with glue, wherein the four rock slabs enclose the first rectangular prism.

15. The method according to claim 6, wherein in the device for measuring the bonding strength between the contaminated rock surface and the solidified material, sealing strips are provided between the transverse support plate and the longitudinal support plate, between the transverse support plate and the bottom plate, between the transverse support plate and the upper cover, and between the upper cover and the longitudinal support plate.

16. The method for measuring the bonding strength between the contaminated rock surface and the solidified material according to claim 15, wherein in the step S4, a temperature during solidification of the cementing liquid is increased by heating coils.

17. The method for measuring the bonding strength between the contaminated rock surface and the solidified material according to claim 15, wherein in the step S1, contact positions between each two adjacent rock slabs are bonded with glue, wherein the four rock slabs enclose the first rectangular prism.

18. The method according to claim 6, wherein in the device for measuring the bonding strength between the contaminated rock surface and the solidified material, the transverse support plates and the longitudinal support plates each are provided with a heating coil.

19. The method for measuring the bonding strength between the contaminated rock surface and the solidified material according to claim 18, wherein in the step S4, a temperature during solidification of the cementing liquid is increased by heating coils.

20. The method for measuring the bonding strength between the contaminated rock surface and the solidified material according to claim 18, wherein in the step S1, contact positions between each two adjacent rock slabs are bonded with glue, wherein the four rock slabs enclose the first rectangular prism.

* * * * *